(12) United States Patent
Wright et al.

(10) Patent No.: US 8,790,391 B2
(45) Date of Patent: *Jul. 29, 2014

(54) METHODS AND DEVICES FOR DELIVERING THERAPEUTIC AGENTS TO TARGET VESSELS

(75) Inventors: Carol Wright, Somerset, NJ (US); Gerard H. Llanos, Stewartsville, NJ (US); Ronald Rakos, Monmouth Junction, NJ (US); Kristen King, Hoboken, NJ (US); Robert Falotico, Belle Meade, NJ (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/420,959

(22) Filed: Mar. 15, 2012

(65) Prior Publication Data

US 2012/0172976 A1    Jul. 5, 2012

Related U.S. Application Data

(60) Continuation of application No. 12/792,114, filed on Jun. 2, 2010, now abandoned, which is a division of application No. 12/204,987, filed on Sep. 5, 2008, now abandoned, which is a continuation of application No. 11/555,420, filed on Nov. 1, 2006, now Pat. No. 7,666,222, which is a continuation of application No. 10/951,385, filed on Sep. 28, 2004, now Pat. No. 7,223,286, which is a continuation of application No. 10/408,328, filed on Apr. 7, 2003, now Pat. No. 6,808,536, which is a continuation of application No. 09/874,117, filed on Jun. 4, 2001, now Pat. No. 6,585,764, which is a continuation of application No. 09/061,568, filed on Apr. 16, 1998, now Pat. No. 6,273,913.

(60) Provisional application No. 60/044,692, filed on Apr. 18, 1997.

(51) Int. Cl.
*A61F 2/02* (2006.01)
*A61F 2/82* (2013.01)

(52) U.S. Cl.
USPC .................................................... 623/1.42

(58) Field of Classification Search
USPC ............................................ 623/1.15–1.48
See application file for complete search history.

(56) References Cited

U.S. PATENT DOCUMENTS

| | | |
|---|---|---|
| 4,733,665 A | 3/1988 | Palmaz |
| 5,252,579 A | 10/1993 | Skotnicki et al. |

(Continued)

FOREIGN PATENT DOCUMENTS

| | | |
|---|---|---|
| EP | 0 950 386 | 10/1999 |
| EP | 0 970 711 | 1/2000 |

(Continued)

OTHER PUBLICATIONS

U.S. Appl. No. 95/001,095, filed Oct. 24, 2008, Falotico et al.

(Continued)

*Primary Examiner* — Suzette J Gherbi
(74) *Attorney, Agent, or Firm* — Baker & Hostetler LLP

(57) ABSTRACT

The present disclosure pertains to stents having a coating applied thereto, wherein the coating comprises a biocompatible polymer/drug mixture, as well as devices comprising a metallic stent, a biocompatible polymeric carrier and a drug.

22 Claims, 2 Drawing Sheets

(56) References Cited

U.S. PATENT DOCUMENTS

| | | | |
|---|---|---|---|
| 5,256,790 A | | 10/1993 | Nelson |
| 5,288,711 A | * | 2/1994 | Mitchell et al. .................. 514/56 |
| 5,304,121 A | | 4/1994 | Sahatjian |
| 5,342,348 A | | 8/1994 | Kaplan |
| 5,362,718 A | | 11/1994 | Skotnicki et al. |
| 5,391,730 A | | 2/1995 | Skotnicki et al. |
| 5,441,977 A | | 8/1995 | Russo et al. |
| 5,455,100 A | * | 10/1995 | White ........................... 428/131 |
| 5,464,650 A | | 11/1995 | Berg et al. |
| 5,516,781 A | | 5/1996 | Morris et al. |
| 5,563,145 A | | 10/1996 | Failli et al. |
| 5,578,075 A | | 11/1996 | Dayton |
| 5,591,227 A | | 1/1997 | Dinh et al. |
| 5,624,411 A | | 4/1997 | Tuch |
| 5,624,893 A | * | 4/1997 | Yanni .............................. 514/2.3 |
| 5,665,728 A | * | 9/1997 | Morris et al. .................. 514/291 |
| 5,837,313 A | | 11/1998 | Ding et al. |
| 5,843,172 A | * | 12/1998 | Yan .............................. 623/1.42 |
| 5,891,108 A | * | 4/1999 | Leone et al. .................... 604/264 |
| 6,096,070 A | * | 8/2000 | Ragheb et al. ............... 623/1.39 |
| 6,120,536 A | | 9/2000 | Ding et al. |
| 6,153,252 A | * | 11/2000 | Hossainy et al. .............. 427/2.3 |
| 6,273,913 B1 | * | 8/2001 | Wright et al. ................ 623/1.42 |
| 6,335,029 B1 | | 1/2002 | Kamath et al. |
| 6,585,764 B2 | * | 7/2003 | Wright et al. ................ 623/1.42 |
| 6,808,536 B2 | * | 10/2004 | Wright et al. ................ 623/1.42 |
| 7,101,857 B2 | * | 9/2006 | Sung et al. ....................... 514/26 |
| 7,217,286 B2 | | 5/2007 | Falotico et al. |
| 7,223,286 B2 | * | 5/2007 | Wright et al. ................ 623/1.42 |
| 7,229,473 B2 | | 6/2007 | Falotico et al. |
| 7,666,222 B2 | * | 2/2010 | Wright et al. ................ 623/1.42 |
| 2011/0038760 A1 | * | 2/2011 | Monzyk et al. ................ 422/119 |
| 2011/0065169 A1 | * | 3/2011 | Steen et al. ................ 435/284.1 |
| 2011/0129389 A1 | * | 6/2011 | Brady et al. ..................... 422/48 |
| 2011/0158847 A1 | * | 6/2011 | Charest et al. ................... 422/45 |
| 2011/0290113 A1 | * | 12/2011 | Borenstein et al. ............... 95/54 |

FOREIGN PATENT DOCUMENTS

| | | |
|---|---|---|
| WO | WO 91/12779 | 9/1991 |
| WO | WO 91/17724 | 11/1991 |
| WO | WO 99/55396 | 11/1999 |

OTHER PUBLICATIONS

U.S. Appl. No. 95/001,096, filed Oct. 24, 2008, Falotico et al.

U.S. Appl. No. 95/001,097, filed Oct. 24, 2008, Wright et al.

U.S. Appl. No. 95/001,102, filed Oct. 24, 2008, Falotico et al.

Haase et al., "Acute and One Year Follow-Up Results after Vessel Size Adapted PTCA Using Intracoronary Ultrasound", European Heart Journal, vol. 19, Feb. 1998, pp. 263-272.

Kimura et al., "Three-Year Follow-Up After Implantation of Metallic Coronary-Artery Stents", New England Journal of Medicine, vol. 334, No. 9, Feb. 1996, pp. 561-566.

Van der Giessen et al., "The Multilink Coronary Stent System", Handbook of Coronary Stents, Patrick W. Serruys, ed., University Hospital Dijkzigt, Rotterdam, 1997, pp. 51-61 (Chapter 6).

"Appeals from the United States District Court for the District of Delaware in consolidated case Nos. 07-CV-0333, 07-CV-0348, 07-CV-0409, and 07-CV-0765", United States Court of Appeals for the Federal Circuit, *Boston Scientific v. Johnson & Johnson*, Decided Jun. 7, 2011, 28 pages.

"Judgment in a Civil Case", In the United States District Court for the District of Delaware, Case No. 1:07-cv-00348-SLR, Doc. No. 363, filed Jan. 20, 2010, 7 pages.

"Memorandum Opinion", In the United States District Court for the District of Delaware, Case No. 1:07-cv-00765-SLR, Doc. No. 368, filed Jan. 20, 2010, 35 pages.

"Order of Judgment", In the United States District Court for the District of New Jersey, Case No. 3:07-cv-05636-JAP-TJB, Doc. No. 137, filed Jan. 27, 2010, 3 pages.

\* cited by examiner

METHODS AND DEVICES FOR DELIVERING THERAPEUTIC AGENTS TO TARGET VESSELS

CROSS-REFERENCE TO RELATED APPLICATIONS

This application is a continuation of U.S. application Ser. No. 12/792,114, filed Jun. 2, 2010, which is a divisional of U.S. application Ser. No. 12/204,987, filed Sep. 5, 2008 (abandoned), which is a continuation of U.S. application Ser. No. 11/555,420, filed Nov. 1, 2006, now U.S. Pat. No. 7,666,222, which in turn is a continuation of Ser. No. 10/951,385, filed Sep. 28, 2004, now U.S. Pat. No. 7,223,286, which is a continuation of Ser. No. 10/408,328, filed Apr. 7, 2003, now issued as U.S. Pat. No. 6,808,536, which is a continuation of application Ser. No. 09/874,117, filed Jun. 4, 2001, now issued as U.S. Pat. No. 6,585,764, which is a continuation of application Ser. No. 09/061,568, filed Apr. 16, 1998, now issued as U.S. Pat. No. 6,273,913, which in turn claims benefit of provisional application Ser. No. 60/044,692, filed Apr. 18, 1997. The disclosures of each of these prior applications are incorporated herein by reference in their entirety.

FIELD OF THE INVENTION

Delivery of rapamycin locally, particularly from an intravascular stent, directly from micropores in the stent body or mixed or bound to a polymer coating applied on stent, to inhibit neointimal tissue proliferation and thereby prevent restenosis. This invention also facilitates the performance of the stent in inhibiting restenosis.

BACKGROUND OF THE INVENTION

Re-narrowing (restenosis) of an artherosclerotic coronary artery after percutaneous transluminal coronary angioplasty (PTCA) occurs in 10-50% of patients undergoing this procedure and subsequently requires either further angioplasty or coronary artery bypass graft. While the exact hormonal and cellular processes promoting restenosis are still being determined, our present understanding is that the process of PTCA, besides opening the artherosclerotically obstructed artery, also injures resident coronary arterial smooth muscle cells (SMC). In response to this injury, adhering platelets, infiltrating macrophages, leukocytes, or the smooth muscle cells (SMC) themselves release cell derived growth factors with subsequent proliferation and migration of medial SMC through the internal elastic lamina to the area of the vessel intima. Further proliferation and hyperplasia of intimal SMC and, most significantly, production of large amounts of extracellular matrix over a period of 3-6 months results in the filling in and narrowing of the vascular space sufficient to significantly obstruct coronary blood flow.

Several recent experimental approaches to preventing SMC proliferation have shown promise althrough the mechanisms for most agents employed are still unclear. Heparin is the best known and characterized agent causing inhibition of SMC proliferation both in vitro and in animal models of balloon angioplasty-mediated injury. The mechanism of SMC inhibition with heparin is still not known but may be due to any or all of the following: 1) reduced expression of the growth regulatory protooncogenes c-fos and c-myc, 2) reduced cellular production of tissue plasminogen activator; are 3) binding and dequestation of growth regulatory factors such as fibrovalent growth factor (FGF).

Other agents which have demonstrated the ability to reduce myointimal thickening in animal models of balloon vascular injury are angiopeptin (a somatostatin analog), calcium channel blockers, angiotensin converting enzyme inhibitors (captopril, cilazapril), cyclosporin A, trapidil (an antianginal, antiplatelet agent), terbinafine (antifungal), colchicine and taxol (antitubulin antiproliferatives), and c-myc and c-myb antinsense oligonucleotides.

Additionally, a goat antibody to the SMC mitogen platelet derived growth factor (PDGF) has been shown to be effective in reducing myointimal thickening in a rat model of balloon angioplasty injury, thereby implicating PDGF directly in the etiology of restenosis. Thus, while no therapy has as yet proven successful clinically in preventing restenosis after angioplasty, the in vivo experimental success of several agents known to inhibit SMC growth suggests that these agents as a class have the capacity to prevent clinical restenosis and deserve careful evaluation in humans.

Coronary heart disease is the major cause of death in men over the age of 40 and in women over the age of fifty in the western world. Most coronary artery-related deaths are due to atherosclerosis. Atherosclerotic lesions which limit or obstruct coronary blood flow are the major cause of ischemic heart disease related mortality and result in 500,000-600,000 deaths in the United States annually. To arrest the disease process and prevent the more advanced disease states in which the cardiac muscle itself is compromised, direct intervention has been employed via percutaneous transiuminal coronary angioplasty (PTCA) or coronary artery bypass graft (CABG).

PTCA is a procedure in which a small balloon-tipped catheter is passed down a narrowed coronary artery and then expanded to re-open the artery. It is currently performed in approximately 250,000-300,000 patients each year. The major advantage of this therapy is that patients in which the procedure is successful need not undergo the more invasive surgical procedure of coronary artery bypass graft. A major difficulty with PTCA is the problem of post-angioplasty closure of the vessel, both immediately after PTCA (acute reocclusion) and in the long term (restenosis).

The mechanism of acute reocclusion appears to involve several factors and may result from vascular recoil with resultant closure of the artery and/or deposition of blood platelets along the damaged length of the newly opened blood vessel followed by formation of a fibrin/red blood cell thrombus. Recently, intravascular stents have been examined as a means of preventing acute reclosure after PTCA.

Restenosis (chronic reclosure) after angioplasty is a more gradual process than acute reocclusion: 30% of patients with subtotal lesions and 50% of patients with chronic total lesions will go on to restenosis after angioplasty. While the exact mechanism for restenosis is still under active investigation, the general aspects of the restenosis process have been identified.

In the normal arterial will, smooth muscle cells (SMC) proliferate at a low rate (<0.1%/day; ref). SMC in vessel wall exists in a 'contractile' phenotype characterized by 80-90% of the cell cytoplasmic volume occupied with the contractile apparatus. Endoplasmic reticulum, golgi bodies, and free ribosomes are few and located in the perinuclear region. Extracellular matrix surrounds SMC and is rich in heparin-like glycosylaminoglycans which are believed to be responsible for maintaining SMC in the contractile phenotypic state.

Upon pressure expansion of an intracoronary balloon catheter during angioplasty, smooth muscle cells within the arterial wall become injured. Cell derived growth factors such as platelet derived growth factor (PDGF), basic fibroblast growth factor (bFGF), epidermal growth factor (EGF), etc. released from platelets (i.e., PDGF) adhering to the damaged arterial luminal surface, invading macrophages and/or leukocytes, or directly from SMC (i.e., BFGF) provoke a proliferation and migratory response in medial SMC. These cells undergo a phenotypic change from the contractile phenotyope to a 'synthetic' phenotype characterized by only few contractile filament bundles but extensive rough endoplasmic reticulum, golgi and free ribosomes. Proliferation/migration usually begins within 1-2 days post-injury and peaks at 2 days in the media, rapidly declining thereafter (Campbell et al., In: Vascular Smooth Muscle Cells in Culture, Campbell, J. H. and Campbell, G. R., Eds, CRC Press, Boca.Ratioh, 1987, pp. 39-55); Clowes, A. W. and Schwartz, S. M., Circ. Res. 56:139-145, 1985).

Finally, daughter synthetic cells migrate to the intimal layer of arterial smooth muscle and continue to proliferate. Proliferation and migration continues until the damaged luminal endothelial layer regenerates at which time proliferation ceases within the intima, usually within 7-14 days postinjury. The remaining increase in intimal thickening which occurs over the next 3-6 months is due to an increase in extracellular matrix rather than cell number. Thus, SMC migration and proliferation is an acute response to vessel injury while intimal hyperplasia is a more chronic response. (Liu et al., Circulation, 79:1374-1387, 1989).

Patients with symptomatic reocclusion require either repeat PTCA or CABG. Because 30-50% of patients undergoing PTCA will experience restenosis, restenosis has clearly limited the success of PTCA as a therapeutic approach to coronary artery disease. Because SMC proliferation and migration are intimately involved with the pathophysiological response to arterial injury, prevention of SMC proliferation and migration represents a target for pharmacological intervention in the prevention of restenosis.

SUMMARY OF THE INVENTION

Novel Features and Applications to Stent Technology

Currently, attempts to improve the clinical performance of stents have involved some variation of either applying a coating to the metal, attaching a covering or membrane, or embedding material on the surface via ion bombardment. A stent designed to include reservoirs is a new approach which offers several important advantages over existing technologies.
Local Drug Delivery from a Stent to Inhibit Restenosis In this application, it is desired to deliver a therapeutic agent to the site of arterial injury. The conventional approach has been to incorporate the therapeutic agent into a polymer material which is then coated on the stent. The ideal coating material must be able to adhere strongly to the metal stent both before and after expansion, be capable of retaining the drug at a sufficient load level to obtain the required dose, be able to release the drug in a controlled way over a period of several weeks, and be as thin as possible so as to minimize the increase in profile. In addition, the coating material should not contribute to any adverse response by the body (i.e., should be non-thrombogenic, non-inflammatory, etc.). To date, the ideal coating material has not been developed for this application.

An alternative would be to design the stent to contain reservoirs which could be loaded with the drug. A coating or membrane of biocompatable material could be applied over the reservoirs which would control the diffusion of the drug from the reservoirs to the artery wall.

One advantage of this system is that the properties of the coating can be optimized for achieving superior biocompatibility and adhesion properties, without the addition requirement of being able to load and release the drug. The size, shape, position, and number of reservoirs can be used to control the amount of drug, and therefore the dose delivered.

BRIEF DESCRIPTION OF THE DRAWINGS

The invention will be better understood in connection with the following figures in which.

DETAILED DESCRIPTION OF ILLUSTRATIVE EMBODIMENTS

Figure 1:
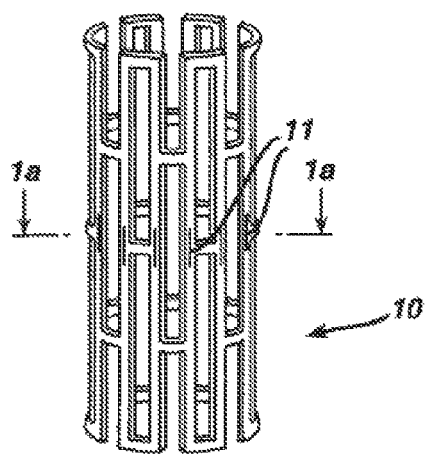
FIGS. 1 and 1a are top views and section views of a stent containing reservoirs as described in the present invention.

Pharmacological attempts to prevent restenosis by pharmacologic means have thus far been unsuccessful and all involve systemic administration of the trial agents. Neither aspirin-dipyridamole, ticlopidine, acute heparin administration, chronic warfarin (6 months) nor methylprednisolone have been effective in preventing restenosis although platelet inhibitors have been effective in preventing acute reocclusion after angioplasty. The calcium antagonists have also been unsuccessful in preventing restenosis, although they are still under study. Other agents currently under study include thromboxane inhibitors, prostacyclin mimetics, platelet membrane receptor blockers, thrombin inhibitors and angiotensin converting enzyme inhibitors. These agents must be given systemically, however, and attainment of a therapeutically effective dose may not be possible; antiproliferative (or anti-restenosis) concentrations may exceed the known toxic concentrations of these agents so that levels sufficient to produce smooth muscle inhibition may not be reached (Lang et al., 42 Ann. Rev. Med., 127-132 (1991); Popma et al., 84 Circulation, 1426-1436 (1991)).

Additional clinical trials in which the effectiveness for preventing restenosis of dietary fish oil supplements, thromboxane receptor antagonists, cholesterol lowering agents, and serotonin antagonists has been examined have shown either conflicting or negative results so that no pharmacological agents are as yet clinically available to prevent post-angioplasty restenosis (Franklin, S. M. and Faxon, D. P., 4 Coronary Artery Disease, 2-32-242 (1993); Serruys, P. W. et al., 88 Circulation, (part 1) 1588-1601, (1993).

Conversely, stents have proven useful in preventing reducing the proliferation of restenosis. Stents, such as the stent 10 seen in layout in FIG. 4, balloon-expandable slotted metal tubes (usually but not limited to stainless steel), which when expanded within the lumen of an angioplastied coronary artery, provide structural support to the arterial wall. This support is helpful in maintaining an open path for blood flow. In two randomized clinical trials, stents were shown to increase angiographic success after PTCA, increase the stenosed blood vessel lumen and to reduce the lesion recurrence at 6 months (Serruys et al., 331 New Eng Jour. Med, 495, (1994); Fischman et al., 331 New Eng Jour. Med, 496-501 (1994). Additionally, in a preliminary trial, heparin coated stents appear to possess the same benefit of reduction in stenosis diameter at follow-up as was observed with non-heparin coated stents. Additionally, heparin coating appears to have the added benefit of producing a reduction in sub-acute thrombosis after stent implantation (Serruys et al., 93 Circulation, 412-422, (1996). Thus, 1) sustained mechanical expansion of a stenosed coronary artery has been shown to provide some measure of restenosis prevention, and 2) coating of stents with heparin has demonstrated both the feasibility and the clinical usefulness of delivering drugs to local, injured tissue off the surface of the stent.

Numerous agents are being actively studied as antiproliferative agents for use in restenosis and have shown some activity in experimental animal models. These include: heparin and heparin fragments (Clowes and Karnovsky, 265 Nature, 25-626, (1977); Guyton, J. R. et al. 46 Circ. Res., 625-634, (1980); Clowes, A. W. and Clowes, M. M., 52 Lab. Invest., 611-616, (1985); Clowes, A. W. and Clowes, M. M., 58 Circ. Res., 839-845 (1986);. Majesky et al., 61 Circ Res., 296-300, (1987); Snow et al., 137 Am. J. Pathol., 313-330 (1990); Okada, T. et al., 25 Neurosurgery, 92-898, (1989) colchicine (Currier, J. W. et al., 80 Circulation, 11-66, (1989), taxol (ref), agiotensin converting enzyme (ACE) inhibitors (Powell, J. S. et al., 245 Science, 186-188 (1989), angiopeptin (Lundergan, C. F. et al., 17 Am. J. Cardiol. (Suppi. B); 132B-136B (1991), Cyclosporin A (Jonasson, L. et. al., 85 Proc. Nati, Acad. Sci., 2303 (1988), goat-anti-rabbit PDGF antibody (Ferns, G. A. A., et al., 253 Science, 1129-1132 (1991), terbinafine (Nemecek, G. M. et al., 248 J. Pharmacol. Exp. Thera., 1167-11747 (1989), trapidil (Liu, M. W. et al., 81 Circulation, 1089-1093 (1990), interferon-gamma (Hansson, G. K. and Holm, 84 J. Circulation, 1266-1272 (1991), steroids (Colburn, M. D. et al., 15 J. Vasc. Surg., 510-518 (1992), see also Berk, B. C. et al., 17 J. Am. Coll. Cardiol., 111B-1 17B (1991), ionizing radiation (ref), fusion toxins (ref) antisense oligonucleotides (ref), gene vectors (ref), and rapamycin (see below).

Of particular interest in rapamycin. Rapamycin is a macrolide antibiotic which blocks IL-2-mediated T-cell proliferation and possesses antiinflammatory activity. While the precise mechanism of rapamycin is still under active investigation, rapamycin has been shown to prevent the $G_{.sub.1}$ to 5 phase progression of T-cells through the cell cycle by inhibiting specific cell cyclins and cyclin-dependent protein kinases (Siekierka, Immunol. Res. 13: 110-116, 1994). The antiproliferative action of rapamycin is not limited to T-cells; Marx et al. (Circ Res 76:412-417, 1995) have demonstrated that rapamycin prevents proliferation of both rat and human SMC in vitro while Poon et al. have shown the rat, porcine, and human SMC migratin can also be inhibited by rapamycin (J Clin Invest 98: 2277-2283, 1996). Thus, rapamycin is capable of inhibiting both the inflammatory response known to occur after arterial injury and stent implantation, as well as the SMC hyperproliferative response. In fact, the combined effects of rapamycin have been demonstrated to result in a diminished SMC hyperproliferative response in a rat femoral artery graft model and in both rat and porcine arterial balloon injury models (Gregory et al., Transplantation 55:1409-1418, 1993; Gallo et al., in press, (1997)). These observations clearly support the potential use of rapamycin in the clinical setting of post-angioplasty restenosis.

Although the ideal agent for restenosis has not yet been identified, some desired properties are clear: inhibition of local thrombosis without the risk systemic bleeding complications and continuous and prevention of the dequale of arterial injury, including local inflammation and sustained prevention smooth muscle proliferation at the site of angioplasty without serious systemic complications. Inasmuch as stents prevent at least a portion of the restenosis process, an agent which prevents inflammation and the proliferation of SMC combined with a stent may provide the most efficacious treatment for post-angioplasty restenosis.

Experiments

Agents: Rapamycin (sirolimus) structural analogs (macrocyclic lactones) and inhibitors of cell-cycle progression.

Delivery Methods:

These can vary:

Local delivery of such agents (rapamycin) from the struts of a stent, from a stent graft, grafts, stent cover or sheath.

Involving comixture with polymers (both degradable and nondegrading) to hold the drug to the stent or graft.

or entrapping the drug into the metal of the stent or graft body which has been modified to contain micropores or channels, as will be explained further herein.

or including covalent binding of the drug to the stent via solution chemistry techniques (such as via the Carmeda process) or dry chemistry techniques (e.g. vapour deposition methods such as rf-plasma polymerization) and combinations thereof.

Catheter delivery intravascularly from a tandem balloon or a porous balloon for intramural uptake.

Extravascular delivery by the pericardial route.

Extravascular delivery by the advential application of sustained release formulations.

Uses:

for inhibition of cell proliferation to prevent neointimal proliferation and restenosis.

prevention of tumor expansion from stents.

prevent ingrowth of tissue into catheters and shunts inducing their failure.

1. Experimental Stent Delivery Method—Delivery from Polymer Matrix:

Solution of Rapamycin, prepared in a solvent miscible with polymer carrier solution, is mixed with solution of polymer at final concentration range 0.001 weight % to 30 weight % of drug. Polymers are biocompatible (i.e., not elicit any negative tissue reaction or promote mural thrombus formation) and degradable, such as lactone-based polyesters or copolyesters, e.g., polylactide, polycaprolacton-glycolide, polyorthoesters, polyanhydrides; poly-amino acids; polysaccharides; polyphosphazenes; poly(ether-ester) copolymers, e.g., PEO-PLLA, or blends thereof. Nonabsorbable biocompatible polymers are also suitable candidates. Polymers such as polydimethylsiolxane; poly(ethylene-vingylacetate); acrylate based polymers or copolymers, e.g., poly(hydroxyethyl methylmethacrylate, polyvinyl pyrrolidinone; fluorinated polymers such as polytetrafluoroethylene; cellulose esters.

Polymer/drug mixture is applied to the surfaces of the stent by either dip-coating, or spray coating, or brush coating or dip/spin coating or combinations thereof, and the solvent allowed to evaporate to leave a film with entrapped rapamycin.

2. Experimental Stent Delivery Method—Delivery from Microporous Depots in Stent Through a Polymer Membrane Coating:

Stent, whose body has been modified to contain micropores or channels is dipped into a solution of Rapamycin, range 0.001 wt % to saturated, in organic solvent such as acetone or methylene chloride, for sufficient time to allow solution to permeate into the pores. (The dipping solution can also be compressed to improve the loading efficiency.) After solvent has been allowed to evaporate, the stent is dipped briefly in fresh solvent to remove excess surface bound drug. A solution of polymer, chosen from any identified in the first experimental method, is applied to the stent as detailed above. This outer layer of polymer will act as diffusion-controller for release of drug.

3. Experimental Stent Delivery Method—Delivery via Lysis of a Covalent Drug Tether:

Rapamycin is modified to contain a hydrolytically or enzymatically labile covalent bond for attaching to the surface of the stent which itself has been chemically derivatized to allow covalent immobilization. Covalent bonds such as ester, amides or anhydrides may be suitable for this.

4. Experimental Method--Pericardial Delivery:

A: Polymeric Sheet

Rapamycin is combined at concentration range previously highlighted, with a degradable polymer such as poly(caprolactone-gylcolid-e) or non-degradable polymer, e.g., polydimethylsiloxane, and mixture cast as a thin sheet, thickness range 10.mu. to 1000.mu. The resulting sheet can be wrapped perivascularly on the target vessel. Preference would be for the absorbable polymer.

B: Conformal Coating:

Rapamycin is combined with a polymer that has a melting temperature just above 37° C., range 40°-45° C. Mixture is applied in a molten state to the external side of the target vessel. Upon cooling to body temperature the mixture solidifies conformably to the vessel wall. Both non-degradable and absorbable biocompatible polymers are suitable.

Figure 1A:
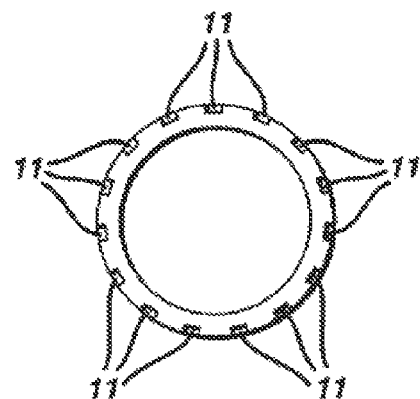
Figure 2A:
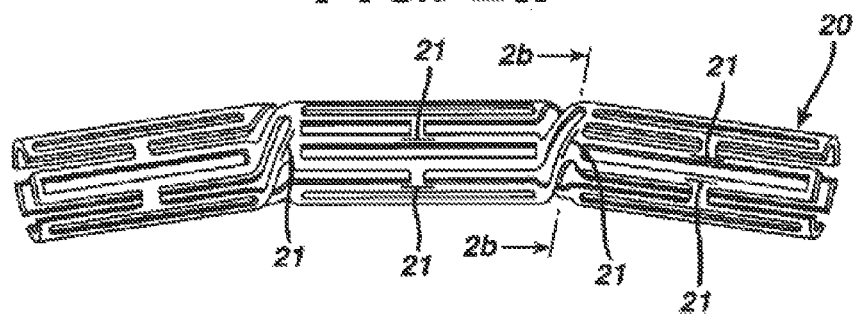
FIGS. 2a and 2b are similar views of an alternate embodiment of the stent with open ends.
Figure 2B:
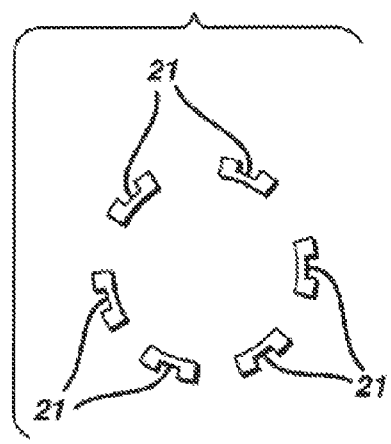
Figure 3A:
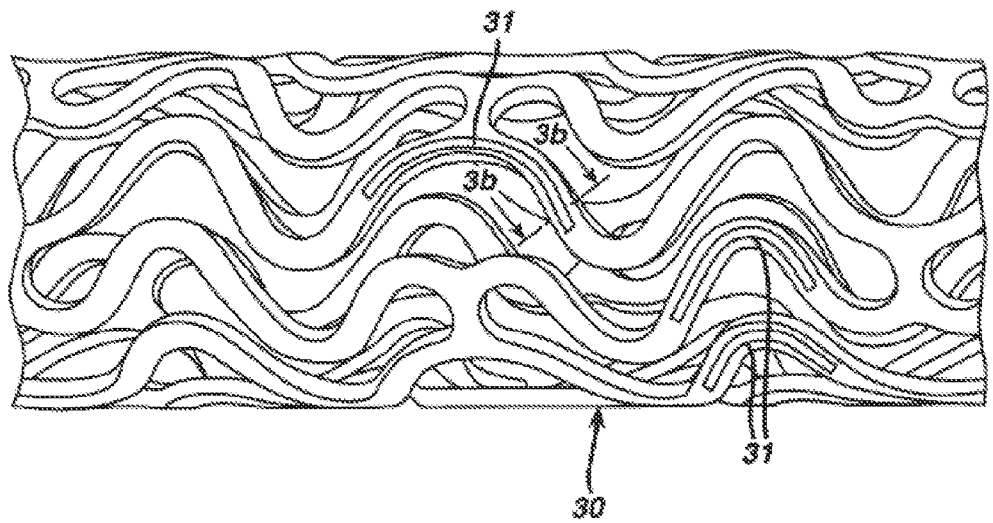
FIGS. 3a and 3b are further alternate figures of a device containing a grooved reservoir.
Figure 3B:
Figure 4:
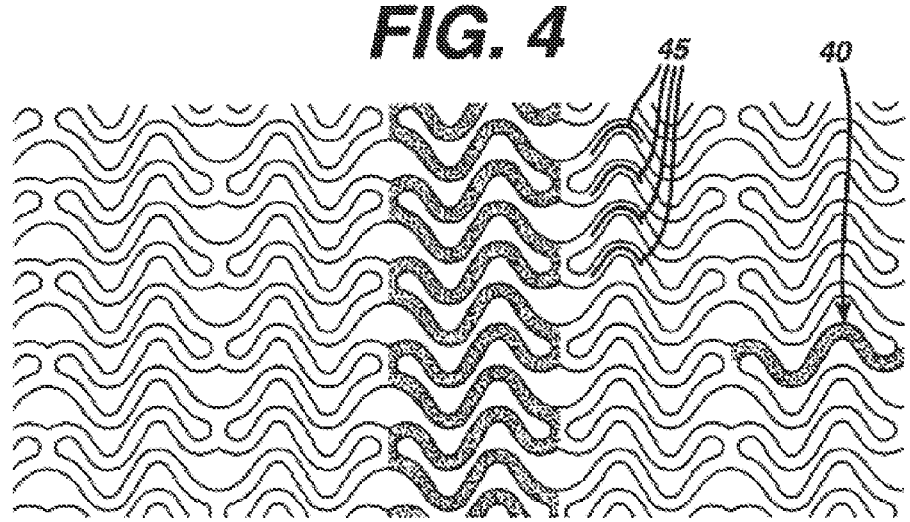
FIG. 4 is a layout view of a device containing a reservoir as in FIG. 3.

As seen in the figures it is also possible to modify currently manufactured stents in order to adequately provide the drug dosages such as rapamycin. As seen in FIGS. 1a, 2a and 3a, any stent strut 10, 20, 30 can be modified to have a certain reservoir or channel 11, 21, 31. Each of these reservoirs can be open or closed as desired. These reservoirs can hold the drug to be delivered. FIG. 4 shows a stent 40 with a reservoir 45 created at the apex of a flexible strut. Of course, this reservoir 45 is intended to be useful to deliver rapamycin or any other drug at a specific point of flexibility of the stent. Accordingly, this concept can be useful for "second generation" type stents.

In any of the foregoing devices, however, it is useful to have the drug dosage applied with enough specificity and enough concentration to provide an effective dosage in the lesion area. In this regard, the reservoir size in the stent struts must be kept at a size of about 0.0005" to about 0.003". Then, it should be possible to adequately apply the drug dosage at the desired location and in the desired amount.

These and other concepts will are disclosed herein. It would be apparent to the reader that modifications are possible to the stent or the drug dosage applied. In any event, however, the any obvious modifications should be perceived to fall within the scope of the invention which is to be realized from the attached claims and their equivalents.

What is claimed:

1. A stent having a coating applied thereto, wherein said coating comprises a biocompatible polymer/drug mixture, said polymer is a nonabsorbable polymer, and said drug is rapamycin and is contained in the coating in weight percentage of about 30%.

2. The stent according to claim 1 comprising a generally thin walled cylinder containing a plurality of generally solid struts to which said coating is applied.

3. The stent according to claim 2 further comprising a channel formed in at least one of said struts.

4. The stent according to claim 3, wherein said channel has a closed perimeter on all sides, an open top and a generally rectangular perimeter, and said channel is smaller in all dimensions than said strut.

5. The stent according to claim 1 wherein the coating is dip-coated onto the stent.

6. The stent according to claim 1 wherein the coating is spray-coated onto the stent.

7. The stent according to claim 1 wherein the coating comprises a polydimethylsiloxane; a poly(ethylene)vinylacetate; a poly(hydroxy)ethylmethylmethacrylate; an acrylate based polymer; an acrylate based copolymer; a polyvinyl pyrrolidone; a cellulose ester; a fluorinated polymer; or a blend thereof.

8. The stent according to claim 7 wherein the coating comprises a fluorinated polymer.

9. The stent according to claim 1 that provides a controlled release of said rapamycin over a period of several weeks.

10. The stent according to claim 1 wherein said rapamycin is present in a therapeutically beneficial amount to inhibit neointimal proliferation.

11. A device comprising a metallic stent, a biocompatible polymeric carrier and a drug that are present in a weight ratio of about 7:3, wherein said polymer is a nonabsorbable polymer, said drug is rapamycin and is present in an amount effective to inhibit neointimal proliferation.

12. The device according to claim 11 wherein said polymeric carrier and drug are mixed together.

13. The device according to claim 11 wherein said polymeric carrier is bound to the drug.

14. The device according to claim 11 wherein the drug is entrapped on the surface of the stent by said polymeric carrier.

15. The device according to claim 11 wherein said stent comprises a generally thin walled cylinder containing a plurality of generally solid struts to which said polymeric carrier and drug are applied.

16. The device according to claim 15 further comprising a channel formed in at least one of said struts.

17. The device according to claim 16, wherein said channel has a closed perimeter on all sides, an open top and a generally rectangular perimeter, and said channel is smaller in all dimensions than said strut.

18. The device according to claim 11 wherein the polymeric carrier and drug are dip-coated onto the stent.

19. The device according to claim 11 wherein the polymeric carrier and drug are spray-coated onto the stent.

20. The device according to claim 11 wherein the polymeric carrier comprises a polydimethylsiloxane; a poly(ethylene)vinylacetate; a poly(hydroxy)ethylmethylmethacrylate; an acrylate based polymer; an acrylate based copolymer; a polyvinyl pyrrolidone; a cellulose ester; a fluorinated polymer; or a blend thereof.

21. The device according to claim 11 wherein the polymeric carrier comprises a fluorinated polymer.

22. The device according to claim 11 that provides a controlled release of said rapamycin over a period of several weeks.

* * * * *